United States Patent
Vegliò et al.

(10) Patent No.: US 7,842,022 B2
(45) Date of Patent: Nov. 30, 2010

(54) DISPOSABLE ABSORBENT ARTICLES WITH IMPROVED PEEL FORCE ON HYDROPHOBIC GARMENT MATERIALS, PARTICULARLY MICROFIBRE MATERIALS

(75) Inventors: Paolo Vegliò, Pescara (IT); Ivano Gagliardi, Pescara (IT); Rodrigo Rosati, Francavilla al Mare (IT); Giovanni Carlucci, Chieti (IT); Roberto D'Addario, Pianella (IT)

(73) Assignee: The Procter & Gamble Company, Cincinnati, OH (US)

( * ) Notice: Subject to any disclaimer, the term of this patent is extended or adjusted under 35 U.S.C. 154(b) by 267 days.

(21) Appl. No.: 11/073,959

(22) Filed: Mar. 7, 2005

(65) Prior Publication Data

US 2005/0203478 A1    Sep. 15, 2005

(30) Foreign Application Priority Data

Mar. 9, 2004    (EP) ................................. 04005535

(51) Int. Cl.
*A61F 13/15* (2006.01)
*A61F 13/20* (2006.01)

(52) U.S. Cl. ....................................... 604/387; 604/386
(58) Field of Classification Search ......... 604/386–387, 604/358, 385.01, 385.03
See application file for complete search history.

(56) References Cited

U.S. PATENT DOCUMENTS

| | | | |
|---|---|---|---|
| 2,736,721 A | 2/1956 | Dexter | |
| 2,814,601 A | 11/1957 | Keil et al. | |
| 3,672,371 A * | 6/1972 | Roeder | 604/387 |
| 4,136,699 A | 1/1979 | Collins et al. | |
| 4,576,597 A | 3/1986 | Hlaban | |
| 4,584,355 A | 4/1986 | Blizzard et al. | |
| 4,585,836 A | 4/1986 | Homan et al. | |
| 4,655,767 A | 4/1987 | Woodard et al. | |
| 4,771,891 A * | 9/1988 | Sorensen et al. | 206/459.5 |
| 4,865,920 A * | 9/1989 | Sweet | 428/447 |
| 5,578,319 A | 11/1996 | Noel | |
| 5,681,305 A | 10/1997 | Korpman | |
| 5,807,367 A | 9/1998 | Dilnik et al. | |

(Continued)

FOREIGN PATENT DOCUMENTS

EP    0 140 135 A1    5/1985

(Continued)

OTHER PUBLICATIONS

PCT International Search Report dated Jun. 15, 2005.

(Continued)

*Primary Examiner*—Melanie J Hand
(74) *Attorney, Agent, or Firm*—Amanda T. Barry; Andrew J. Hagerty; Gary J. Foose

(57) ABSTRACT

The present invention relates to an absorbent article for personal hygiene, especially a sanitary napkin, panty liner and the like, comprising an adhesive for securing said article to the garments of a wearer. Said adhesive is capable to establish a bonding of the garment-facing surface of said absorbent article to the garment of the wearer, which is able to resist a peel force of at least 0.6 N per 5 cm, according to the test method herein, on a reference microfiber substrate.

19 Claims, 3 Drawing Sheets

U.S. PATENT DOCUMENTS

| | | |
|---|---|---|
| 6,213,993 B1 | 4/2001 | Zacharias et al. |
| 6,277,106 B1 * | 8/2001 | Boudry et al. ............... 604/394 |
| 6,316,524 B1 | 11/2001 | Corzani et al. |
| 6,613,175 B1 | 9/2003 | Moscherosch et al. |
| 6,641,569 B1 | 11/2003 | Coles et al. |
| 6,921,574 B2 | 7/2005 | Cinelli et al. |
| 7,163,740 B2 | 1/2007 | Rosati et al. |
| 2003/0187115 A1 | 10/2003 | Cinelli et al. |
| 2003/0212416 A1 | 11/2003 | Cinelli et al. |
| 2004/0134596 A1 | 7/2004 | Rosati et al. |
| 2004/0142110 A1 | 7/2004 | Branca et al. |
| 2005/0203478 A1 | 9/2005 | Veglio |

FOREIGN PATENT DOCUMENTS

| | | |
|---|---|---|
| JP | UM S61-168103 | 10/1986 |
| JP | H07-328068 | 12/1995 |
| SE | 374 489 | 3/1975 |
| WO | WO 00/23122 | 4/2000 |
| WO | WO 00/61054 | 10/2000 |
| WO | WO 02098999 A2 * | 12/2002 |

OTHER PUBLICATIONS

Decision on Appeal for U.S. Appl. No. 11/074,916 dated Jul. 27, 2009; P&G Case CM2825; Rosati et al.; filing date Mar. 8, 2005.

* cited by examiner

DISPOSABLE ABSORBENT ARTICLES WITH IMPROVED PEEL FORCE ON HYDROPHOBIC GARMENT MATERIALS, PARTICULARLY MICROFIBRE MATERIALS

FIELD OF THE INVENTION

The present invention relates to an absorbent article for personal hygiene, especially a sanitary napkin, panty liner and the like, comprising an adhesive for securing said article to the garments of a wearer. Said adhesive is capable to establish a bonding of the garment-facing surface of said absorbent article to the garment of the wearer, which is able to resist a peel force of at least 0.6 N per 5 cm, according to the test method herein, on a reference microfibre substrate.

BACKGROUND OF THE INVENTION

The use of adhesives for securing disposable absorbent articles for personal hygiene is well known in the art. In particular, the use of hot melt and emulsion-based adhesives is general technical standard. The application of emulsion-based adhesives onto the backsheets of absorbent articles for garment fastening is for instance known from SE-A-374,489. The use of hot melt adhesives for this purpose is for instance described in EP-A-140,135 or in WO 00/61054.

In the recent time a significant change with respect to the clothing habits of women could be noticed. An increasing share of especially younger women does not wear cotton panties anymore, which were the standard of the last decades, but more and more tends to wear panties consisting of a particular synthetic fabric material, which is commonly referred to as "micro-fibre".

Micro fibres are one of the recent major developments in the fabric industry. These fibres conventionally have less than 1 denier and a diameter in cross section of conventionally not more than 10 µm. Soon after their occurrence on the market micro fibres have found use in especially the clothing industry, where they are used to form fabrics having unique physical and mechanical performance, such as luxurious look and feel due to the fact that microfibres are even thinner than silk, together with very good strength, uniformity and processing characteristics. The resulting very fine and close woven and knitted fabrics are characterized by soft handle and breathability. Due to this, microfibre fabrics are also used for the production of underpants for women, especially fashionable ones for younger women.

Microfibre fabrics have very different physical characteristics compared to conventional cotton fabrics. This especially applies to hydrophobicity, which is higher for microfibres and is oftentimes even increased by the treatment of the microfibres with fluoropolymers, silicones, microwaxes and the like. Thus, unlike conventional cotton garments, microfibre garments are provided with a substantially hydrophobic surface. Furthermore, the density of the fabrics made of microfibres is significantly higher compared to those made of cotton. As a consequence, the void space between the individual microfibre filaments is much lower compared to the void space in cotton fabrics. Because of the aforementioned characteristics currently available conventional adhesives for fastening absorbent articles, such as sanitary napkins and panty liners, to garments do not work satisfactory for microfibre garments. It has been observed that the bonding forces the panty fastening adhesives (hereinafter PFAs) used in commercially available absorbent articles for personal hygiene (e.g. feminine hygiene) are able to deliver on microfibre garments are by far too low for reliable attachment of absorbent articles to such microfibre garments, especially under stress conditions, such as for instance during physical exercise and the like.

It is therefore an object of the present invention to provide an absorbent article with a PFA, which is capable to provide secure attachment of the absorbent article on microfibre-based garments.

It is a further object of the present invention to provide an absorbent article with a PFA having improved garment compatibility by being capable to provide secure attachment of the absorbent article on all kinds of garments, particularly cotton-based garments and microfibre-based garments.

SUMMARY OF THE INVENTION

The present invention provides an absorbent article being provided with a adhesive for attachment to the garments of a wearer. In particular, the absorbent article of the present invention is provided with an adhesive on its garment-facing surface, the adhesive providing a peel force of at least 0.6 N per 5 cm according to the test method described herein when joining the article to a reference microfibre substrate. Preferably the adhesive is present on the garment-facing surface of the article at a basis weight of from 1 to 35 g/m². Furthermore, the adhesive is preferably present on the garment-facing surface of the article at a surface coverage of at least 30%.

In a specific embodiment the present invention provides an absorbent article being provided with a two-component adhesive system on the garment-facing surface, comprising the aforementioned adhesive and additionally another adhesive providing a peel force of 0.6 N per 5 cm on a reference cotton substrate according to the test method herein. Preferably the second adhesive is present on the garment-facing surface of the article at a basis weight of from 1 to 35 g/m². Furthermore, the second adhesive is preferably present on the garment-facing surface of the article at a surface coverage of at least 30%.

BRIEF DESCRIPTION OF THE DRAWINGS

FIGS. 1-3 illustrate conventional feminine care articles, whereas FIG. 4 illustrates a so-called "Tanga"-liner.

FIG. 6 represents a conventional panty liner and FIG. 7 represents a panty liner for tanga undergarments.

DETAILED DESCRIPTION OF THE INVENTION

Figure 1:
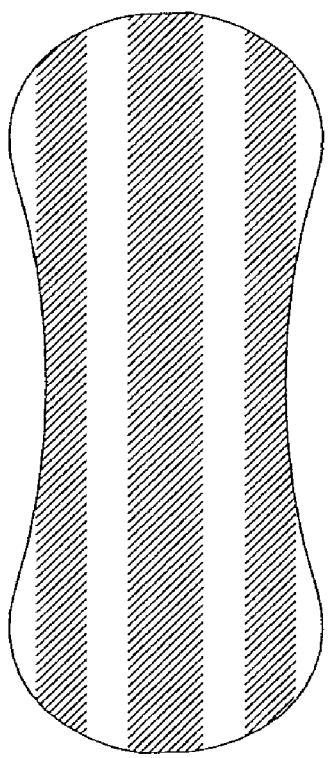
FIGS. 1-4 illustrate embodiments, where the PFA according to the present invention is applied onto the garment-facing surface of the absorbent article, typically the backsheet, in the form of stripes.
Figure 2:
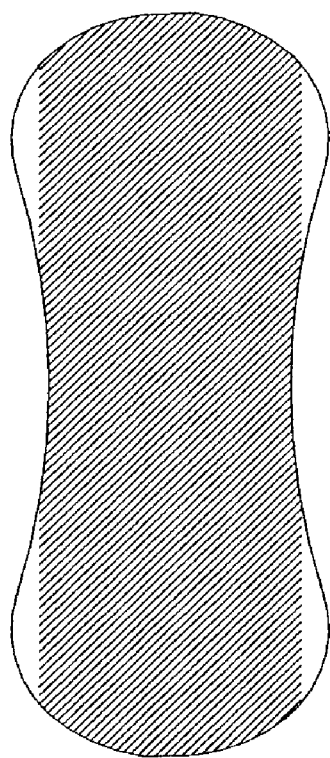
Figure 3:
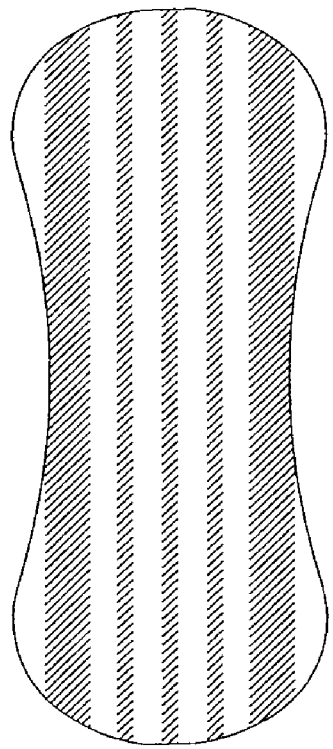
Figure 4:
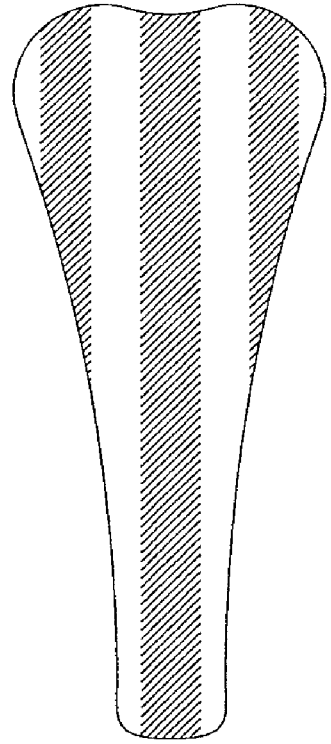

The term 'absorbent article' is used herein in a very broad sense including any article being able to receive and/or absorb and/or contain and/or retain fluids and/or exudates, especially bodily fluids/bodily exudates. The absorbent article, which is referred to in the present invention typically comprises a fluid pervious topsheet as the wearer-facing surface, a fluid impervious backsheet as the garment-facing surface that is preferably water vapour and/or gas pervious and an absorbent core comprised there between. Furthermore, absorbent articles in the context of the present invention are provided with a means for their attachment to the user's garment, in particular with an adhesive. Preferred absorbent articles in the context of the present invention are disposable absorbent articles. Typical disposable absorbent articles according to the present invention are absorbent articles for personal hygiene, such as baby care articles like baby diapers; incontinence pads and perspiration pads like underarm sweat pads or hat bands. Particularly preferred disposable absorbent articles are absorbent articles for feminine hygiene like sanitary napkins and panty liners.

By 'body fluid' it is meant herein any fluid produced by the human body including for instance perspiration, urine, blood, menstrual fluids, vaginal secretions and the like.

The term 'disposable' is used herein to describe articles, which are not intended to be laundered or otherwise restored or reused as an article (i.e. they are intended to be discarded after a single use and preferably to be recycled, composted or otherwise disposed of in an environmentally compatible manner).

The term 'use', as used herein, refers to the period of time that starts when the absorbent article is actually put in contact with the anatomy of the user.

As used herein, 'hydrophilic' refers to a material having a contact angle of water in air of less than 90 degrees, whereas the term 'hydrophobic' herein refers to a material having a contact angle of water in air of 90 degrees or greater. Hydrophobic materials are also referred to as water-repellent.

'Microfibres' as referred to herein means fibres having a denier of not more than 1 (1 denier=1 g/9000 m of fibre) and a diameter in cross section of not more than 10 µm. Microfibres are artificial man-made fibres and most typically consist of polyester or polyamides, such as nylon. Microfibres are used by the fabric industry for making very fine close woven fabric materials and knitted fabrics, which are characterized by soft handle and breathability. Microfibre fabrics have very different physical characteristics compared to conventional cotton fabrics. This especially applies for hydrophobicity, which is significantly higher than the one of cotton fibres and which oftentimes is even increased by the treatment of the microfibres with fluoropolymers, silicones, microwaxes and the like. Oftentimes microfibre garments also contain elastan/Lycra fibres for providing elasticity. Due to the small diameter of the microfibres the density of the fabrics made therefrom is very high compared to the one of cotton fabrics. Thanks to the small fibre diameter of those microfibres the void space between the individual microfibres is very low compared to cotton fabrics. Typical microfibre materials are marketed by e.g. DuPont under the trade name Tactel® or by Nylstar under the trade name Meryl®.

As said infra, an absorbent article in the context of the present invention comprises an adhesive means for the attachment of this article to the user's garments. This adhesive is also referred to as 'panty fastening adhesive' or 'PFA'. The PFA is provided on the garment facing surface of the absorbent article of the present invention, typically the backsheet, for attaching said article to the garment of a wearer. Similarly, if the product is a winged product, the wings can also be provided with PFA on the garment-facing surface in order to secure the wings to the wearer's garment. The PFA for use herein is preferably a pressure-sensitive adhesive, with hot melt pressure-sensitive adhesives being particularly preferred.

As an essential feature the absorbent article of the present invention comprises at least one PFA (hereinafter adhesive A) with improved bonding properties towards microfibre garments. Said adhesive A provides a peel force of at least 0.6 N per 5 cm according to the peel force test method as described herein when joining the article to a standard microfibre material.

Preferably, the adhesive A provides a peel force of at least 0.8 N, more preferably 1 N, even more preferably 1.2 N and most preferably 2.4 N per 5 cm on the reference microfibre substrate according to the peel force test method as described herein under the aforementioned conditions.

'Surface coverage' of a surface as used herein means that said surface is covered by a material to a certain percentage. For instance, 30% PFA surface coverage of the garment facing surface of the absorbent article herein means that 30% of the total garment-facing surface of the absorbent article is covered with PFA. The garment-facing surface of the article of the present invention can be covered with the PFA in a continuous manner, i.e. a continuous coating of the whole garment-facing surface, or in a discontinuous manner, such as by stripes, dots or very fine droplets of PFA. For surface coverage herein the part of the garment-facing surface of the article, which is actually covered by PFA material is taken.

Preferably adhesive A has a surface coverage on the garment-facing surface of the article of at least 30%, preferably 40%, more preferably 50%, even more preferably 60% and most preferably 70-100% in order to achieve sufficient PFA-coated area on the garment-facing surface of the absorbent article of the present invention for making the bond to the garment material.

Preferably adhesive A is present on the garment-facing surface of the article at a basis weight of from 1 to 35 $g/m^2$, preferably 10-30 $g/m^2$ and more preferably 15-25 $g/m^2$.

In a preferred embodiment herein the adhesive A provides a peel force on a reference cotton substrate, which is up to 5 times higher than, preferably up to 4 times higher than, more preferably up to 3 times higher than and most preferably equals the peel force it provides on a standard microfibre substrate, when present at the same basis weight, according to the test method herein.

In the following, examples for adhesives suitable to be used as adhesive A for secure attachment of an absorbent article to a microfibre substrate are listed:

A suitable class of pressure sensitive adhesive compositions is disclosed in U.S. Pat. No. 4,865,920 and consists of (i) a trimethylsilyl-endblocked polysilicate resin such as a silicone resin consisting of a benzene-soluble resinous copolymer containing silicon-bonded hydroxyl radicals and consisting essentially of triorganosiloxy units of the formula $R_3SiO_{1/2}$ and tetrafunctional-siloxy units of the formula $SiO_{4/2}$ in a ratio of about 0.6 to 0.9 triorganosiloxy units for each tetrafunctionalsiloxy unit present in the copolymer and (ii) a silanol-endstopped polydiorganosiloxane fluid (silicone fluid), e.g. a polydimethylsiloxane fluid. U.S. Pat. No. 2,736,721 to Dexter et al. and U.S. Pat. No. 2,814,601, to Currie et al. teach such or similar pressure sensitive adhesive compositions.

Another class of suitable pressure sensitive adhesive compositions to use with the specific ester disclosed herein supra, is that or those similar to that of U.S. Pat. No. 2,857,356 to Goodwin, Jr. The Goodwin, Jr. patent teaches silicone pressure sensitive adhesive compositions which consist of a mixture of ingredients comprising (i) a cohydrolysis product of a trialkyl hydrolyzable silane and alkyl silicate, wherein the cohydrolysis product contains a plurality of silicon-bonded hydroxy groups (silicone resin), and (ii) a linear, high viscosity organopolysiloxane fluid (silicone fluid) containing silicon-bonded hydroxy groups.

The silicone resin (i) and the silicone fluid (ii) may optionally be condensed together such as by the procedure described in Canadian Patent No. 711,756 to Pail. In such a condensation reaction, the silicone resin (i) and the silicone fluid (ii) are mixed together in the presence of a silanol condensation catalyst and the silicone resin (i) and the silicone fluid (ii) are condensed, for example, by heating under reflux condition for 1 to 20 hours. Examples of silanol condensation catalysts are primary, secondary and tertiary amines, carboxylic acids of these amines and quaternary ammonium salts.

Another class of suitable pressure sensitive adhesive compositions to use with the specific ester disclosed herein supra are those compositions described in U.S. Pat. Nos. 4,591,622 and 4,584,355 to Blizzard et al. U.S. Pat. No. 4,585,836 to Homan et al. and U.S. Pat. No. 4,655,767 to Woodard et al. Generally, these pressure sensitive adhesive compositions consist of a blend of a i) a silicone resin and ii) a silicone fluid which are chemically treated so as to reduce the silicon-bonded hydroxyl content of the blend. These compositions may optionally be condensed as described immediately above prior to the chemical treatment.

The silicone pressure sensitive adhesive is prepared by merely mixing siloxanes (i) and (ii) with the selected ester or esters. The silicone pressure sensitive adhesive compositions are then heated to a coatable viscosity and coated on the garment-facing surface of the absorbent article. Optionally, the coated silicone pressure sensitive adhesive may be cured. When the silicone pressure sensitive adhesive is to be cured, it may further contain a curing catalyst. It is preferred that such catalysts remain inactive at room temperature and temperatures reached during the hot-melt coating process. Therefore, such catalysts that either become active at temperatures higher than that of the hot-melting temperatures or become active upon exposure to another energy source, e.g. UV light or electron beam radiation, are suitable.

Optionally, the silicone pressure sensitive adhesive may include fillers, such as extending or reinforcing fillers.

The ester used for making the silicone pressure sensitive adhesive disclosed in U.S. Pat. No. 2,857,356 to Goodwin as described supra has the general formula:

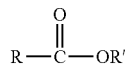

wherein R is a monovalent hydrocarbon radical having from 2 to 32 carbon atoms and R' is a monovalent hydrocarbon radical having from 1 to 14 carbon atoms. Preferably, R has from 10 to 19 carbon atoms and R' has from 1 to 3 carbon atoms. R and R' are selected independently, so that they may be the same or different.

Preferably, the esters for the hot-melt silicone pressure sensitive adhesives are not flammable which affords a safer procedure during application of the silicone pressure sensitive adhesive compositions at elevated temperatures. Flammable materials, as the term is used herein, are those materials, which are flammable according to the definition provided in United States Code of Federal Regulations, Title 49, Part 173, Section 115 (49 CFR 173.115). Briefly restated, a flammable liquid means any liquid having a flash point below 100° F. (37.8° C.), where flash point means the minimum temperature at which a liquid gives off vapour within a test vessel in sufficient concentration to form an ignitable mixture with air near the surface of the liquid. The CFR provides proper testing conditions for measuring flash point. If flammable esters are used, the coating operation could be done in an inert atmosphere (e.g. nitrogen gas), devoid of oxygen gas to avoid fire hazards.

The ester employed must not boil at the processing temperatures. Typically, temperatures above about 100° C. produce suitable working viscosities with the hot melt silicone pressure sensitive adhesives, therefore, esters having boiling points above 100° C. are preferred. The esters may be solid or liquid. Even though solid esters may be used, they must be at least somewhat soluble in the silicone pressure sensitive adhesive at the coating temperature.

Examples of suitable esters include 1-phenylethylpropionate, linolec acid ethyl ester, dodecyl acetate, ethyl triacontanoate, octyl acetate, methyl caproate, methyl decanoate, isobutyl acetate, methyl docosanoate, methyl heptadeconate, isopropylpalmitate, isopropylmyristate, lauric acid methyl ester and mixtures thereof.

The esters may be employed in amounts of about 1% to 10% by weight based on the total weight of the silicone resin and the silicone fluid. Generally, if the ester is a fluid at room temperature, especially when the pressure-sensitive adhesive is not to be cured, it is preferred that the maximum limit of the ester be about 7%, because at higher amounts, the ester may make the hot-melt silicone pressure sensitive adhesive too flowable at room temperature which is undesirable for most applications. Usually, the solid esters are preferred when it is desired to use greater than about 7% by weight ester in the hot melt silicone pressure sensitive adhesive.

The silicone pressure sensitive adhesives may be made by mixing the ingredients in any order. Reaction or treatment of the ingredients, e.g. condensing according to the procedure disclosed in CA 711,756 or chemically treating according to U.S. Pat. No. 4,591,622 and U.S. Pat. No. 4,584,355 may require completion prior to the addition of the ester.

The ester allows the hot melt silicone pressure sensitive adhesive to decrease in viscosity with elevated temperatures to a suitable viscosity for coating a substrate without the use of solvents that must be removed. Suitable viscosities for hot-melting processing are about 20,000-30,000 cp (centipoise) and, more typically, 30,000-40,000 cp. Typically, heating the hot-melt silicone pressure sensitive adhesives of this invention to temperatures of about 100° C. or more (more typically above 150° C.) result in suitable viscosities less than 40,000 cp. These coatable temperatures are low enough so that decomposition of the composition does not occur. Lower temperatures may result in coatable viscosities depending on the coating equipment used, the desired end product and the type and amount of ester used. For example, the thicker the layer of pressure sensitive adhesive desired, the higher the coating viscosity can be.

An exemplary adhesive A suitable for use herein of the above class of adhesives is Bio PSA 7-4560 available from Dow Corning.

An exemplary adhesive A suitable for use herein of another class of adhesives, based on block copolymers, is MF-55 available from Savare.

In a preferred embodiment of the present invention the absorbent article is provided with a multi-component adhesive system comprising at least a second PFA besides said adhesive A. Preferred as second PFA (adhesive B hereinafter) are those PFAs with excellent bonding properties towards cotton garments. Said adhesive B provides a peel force of at least 0.6 N per 5 cm when joining the article to a reference cotton material according to the test method herein.

Preferably said multi-component adhesive system has a combined surface coverage on the garment-facing surface of the article of at least 30%, preferably 40%, more preferably 50%, even more preferably 60% and most preferably 70-100% in order to achieve sufficient PFA-coated area on the garment-facing surface of the absorbent article of the present invention for making the bond to the garment material. 'Combined surface coverage' herein means the added surface coverage for adhesives A and B. It is further preferred that said multi-component adhesive system comprises adhesives A and B at equal surface coverage.

Preferably multi-component adhesive system is present on the garment-facing surface of the article at a combined basis weight of from 1 to 35 g/m$^2$, preferably 10-30 g/m$^2$ and more preferably 15-25 g/m$^2$. 'Combined basis weight' herein means the added basis weight for adhesives A and B. It is further preferred that said multi-component adhesive system comprises adhesives A and B at equal basis weight.

Examples of adhesive B are conventional PFAs known in the art, which are not capable to fulfil the peel force criterion on standard microfibre material according to the present invention are HL 1461E available from Fuller or DM0110 available from National Starch. However, these PFAs have very good bonding performance on cotton-based materials, which renders them suitable as adhesive B according to the aforementioned embodiment.

At least one and preferably all PFAs present on the garment-facing surface of the absorbent article of the present invention are hot melt adhesives.

Figure 5:
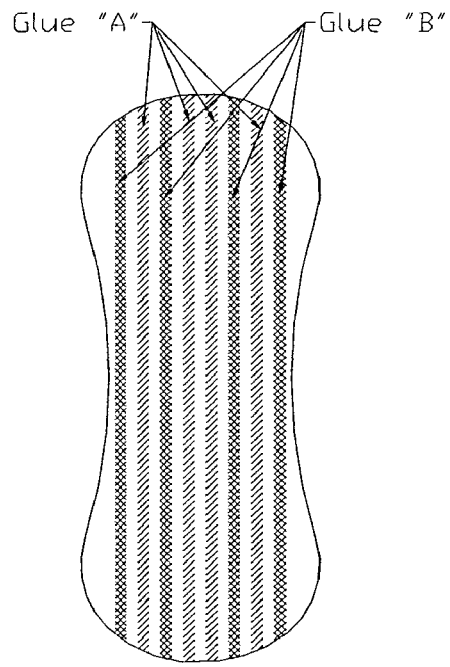
FIG. 5 illustrates an embodiment with alternating lines of two different PFAs.
Figure 6:
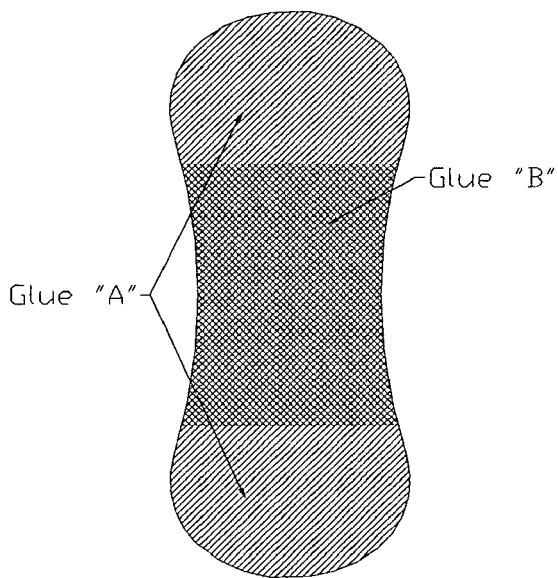
FIGS. 6 and 7 illustrate embodiments, where one adhesive is coated onto the central region of the garment-facing surface of the absorbent article and another adhesive is coated onto the end region(s) of said garment-facing surface of the absorbent article.
Figure 7:
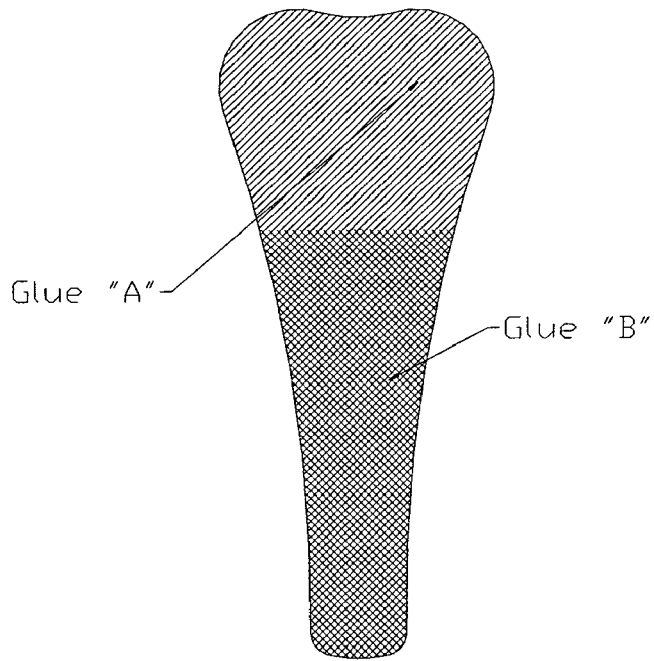

It is also within the scope of the present invention to apply the PFA in patterns onto the garment-facing surface of the absorbent article of the present invention. There are embodiments herein, there the PFA covers the whole garment-facing surface of the absorbent article as a continuous layer. In other embodiments herein the PFA or the PFAs, if there is more than one PFA coated onto the garment-facing surface of the absorbent article, are printed in patterns, such as stripes. These stripes can be alternating, can have variable width and can be spaced apart from each other by variable distance. FIGS. 1-4 illustrate embodiments, where one PFA was applied onto the garment-facing surface of the absorbent article in the form of stripes. FIG. 5 illustrates an embodiment with alternating lines of two different PFAs. In other embodiments herein one PFA is coated onto the central portion of the garment-facing surface of the absorbent article, whereas another PFA is coated onto the end portions of the garment-facing surface of the absorbent article. Such an embodiment is illustrated by FIGS. 6 and 7. It is, however, also within the scope of the present invention that the PFA is coated onto the garment-facing surface of the absorbent article in a completely random manner, such as for example achieved by spraying processes. Preferably, the requirement that the PFA herein has to have a surface coverage on the garment-facing surface of the article of at least 30%, preferably 40%, more preferably 50%, even more preferably 60% and most preferably 70-100% is met.

The absorbent article of the present invention typically comprises a topsheet as the body-facing surface, a backsheet as the garment-facing surface and an absorbent core disposed therebetween.

The Topsheet

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and non-woven materials can be comprised of natural fibres (e.g., wood or cotton fibres), synthetic fibres (e.g., polymeric fibres such as polyester, polypropylene, or polyethylene fibres) or from a combination of natural and synthetic fibres or bi-/multi-component fibres.

Preferred topsheets for use in the present invention are selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the body remains dry; thereby reducing body soiling and creating a more comfortable feel for the wearer. Suitable formed films are described in U.S. Pat. No. 3,929,135; U.S. Pat. No. 4,324,246; U.S. Pat. No. 4,342,314; U.S. Pat. No. 4,463,045; and U.S. Pat. No. 5,006,394. Particularly preferred micro apertured formed film topsheets are disclosed in U.S. Pat. No. 4,609,518 and U.S. Pat. No. 4,629,643. A preferred topsheet for the present invention comprises the formed film described in one or more of the above patents and marketed on sanitary napkins by The Procter & Gamble Company of Cincinnati, Ohio as "DRI-WEAVE".

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The body surface of the formed film topsheet can be hydrophilic so as to help liquid to transfer though the topsheet faster than if the body surface was not hydrophilic. In a preferred embodiment, surfactant is incorporated into the polymeric materials of the formed film topsheet such as is described in PCT publication WO 93/09741. Alternatively, the body surface of the topsheet can be made hydrophilic by treating it with a surfactant such as is described in U.S. Pat. No. 4,950,254.

Another alternative are so called hybrid topsheets, which incorporate fibrous and film like structures particularly useful embodiments of such hybrid topsheets are disclosed in PCT publications WO 93/09744; WO 93/11725 or WO 93/11726.

The topsheet typically extends across the whole of the absorbent article and outside the area coextensive with the absorbent article. The topsheet can extend and form part or all of the preferred side flaps, side wrapping elements or wings.

When referring to the topsheet a multi layer structure or a monolayer structure is contemplated. The hybrid topsheet mentioned above is such a multi layer design but other multi layer topsheets such as primary and secondary topsheet designs are also considered.

Absorbent Core

According to the present invention the absorbent cores suitable for use herein may be selected from any of the absorbent cores or core system known in the art. As used herein the term absorbent core refers to any material or multiple material layers whose primary function is to absorb, store and distribute fluid.

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. Preferably at least one of said layers comprises absorbent gelling materials usually referred to as "hydrogel", "superabsorbent", "hydrocolloid" materials in combination with suitable carriers.

Backsheet

The backsheet primarily prevents the exudates absorbed and contained in the absorbent article from wetting articles that contact the absorbent product such as underpants, pants, pajamas and garments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent article and can extend into and form part of or all of the preferred sideflaps, side wrapping elements or wings.

According to the present invention the backsheet of the absorbent article is preferably breathable such that it is moisture vapour permeable and thus comprises at least one gas permeable layer. Suitable gas permeable layers include 2 dimensional, planar micro and macro-porous films, macroscopically expanded films, formed apertured films and monolithic films. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable 2 dimensional planar layers of the backsheet may be made of any material known in the art, but are preferably manufactured from commonly available polymeric materials. Suitable materials are for example Gortex™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EP 293,482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport towards the core.

Suitable macroscopically expanded films for use herein include films as described in for example in U.S. Pat. No. 4,637,819 and U.S. Pat. No. 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland such as Pebax™, available from Elf Atochem (France) and Estane™ available from B.F. Goodrich (Belgium).

Particularly preferred backsheets for the present invention comprise at least two layers comprising at least one layer selected from the above, such as microporous and apertured formed films and an additional layer which may also be selected from the above listed backsheets or may be a fibrous woven or nonwoven. The most preferred breathable backsheet component comprises a microporous film and an apertured formed film or a microporous and a hydrophobic woven or nonwoven material. Another particularly preferred class of backsheets for use herein are combinations of films and nonwovens.

The adhesive-coated surfaces are typically provided with protective covers, which are removed prior to use. Prior to use of the absorbent article the areas being coated with PFA are typically protected from contamination and from adhering to another surface, where this is not desired, by a protective cover means such as a silicone coated release paper, a plastic film or any other easily removable cover. The protective cover means can be provided as a single piece or in a multitude of pieces, e.g. to cover the individual adhesive areas. It also can perform other functions such as provide individualised packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The PFA may be applied to the garment-facing surface of the absorbent article, typically the backsheet or the wings using any one of methods well known in the art for this purpose such as slot coating, spraying and roll printing. With the development of adhesive printing as described for example in EP 745,432, EP 745,433, and EP 745,368 it has now also become possible to provide such panty-fastening adhesive in any desired shape and hence these methods are particularly preferred in the present invention. A particularly preferred method of applying the PFA to the garment-facing surface of the absorbent article is printing the PFA onto a release paper, which is then pressed onto the garment-facing surface of the absorbent article. Thereby the PFA is transferred from the release paper to the garment-facing surface of the absorbent article. Such a procedure is described in EP 788,338. Any application pattern known the respective art is suitable for applying the PFA according to the present invention to the garment-facing surface of the absorbent article herein. Illustrative examples are presented in the attached figures. Preferably, the panty fastening adhesive is applied in intermittent patterns such as for example micro-sized intermittent dots, intermittent strips, lines or grids or other designed shapes such as circles. However, also completely random PFA patterns are within the scope of the present invention. As said before, it is preferred that the criterion that the PFA has a surface coverage on the garment-facing surface of the article of at least 30%, preferably 40%, more preferably 50%, even more preferably 60% and most preferably 70-100% is met.

The present invention is further illustrated by the following examples:

Examples

The following examples can be divided into two groups, which differentiate in the backsheet material, on which the PFS was coated.

One sequence of measurements was done on a nonwoven backsheet material, which was a SBPP nonwoven 23 g/m$^2$ from BBA Neuberger available under the code BASE F1 023 01 001. The PFA was applied as a full coating application (50 mm wide and 20 cm long) done directly on the outer surface of the nonwoven backsheet with a PFA basis weight of 17 g/m$^2$ at a coating temperature of 155° C. for Savare MF-55 and Fuller 1461E. The PFA surface coverage for these examples was about 45%. The results are listed in table 1.

A second sequence of measurements was done on a film backsheet material, which was a PE film 25 g/m$^2$ from Britton Taco available under the code ST-012-White. Coating of the PFA onto the outer surface of the backsheet film was facilitated by first applying the PFA onto a release paper, which is available from Akrosil under the code BL XXG NL-MGA SILOX D3H/0 and having a basis weight of 40 g/m$^2$, at an application temperature of 200° C. for Dow Corning BioPSA 7-4560, 155° C. for Fuller HL1461E and 190° C. for National Starch DM0110. After this coating step the PFA-coated release paper was transferred to the outer surface of the backsheet film by pressing the PFA-coated surface of the release paper onto said outer surface at a pressure of 2 bar. Thereby, the PFA was transferred from the release paper to the backsheet film and the release paper was removed afterwards. The result was a full coating application 50 mm wide and 20 cm long at a basis weight of 20 g/m$^2$. The PFA surface coverage for these examples was about 89%. The results are listed in table 2.

TABLE 1 measurements with nonwoven backsheet material

|  | MF-55 | BioPSA 7-4560 | HL1461E | DM0110 |
|---|---|---|---|---|
| Peel force on cotton [N/5 cm] | 1.96 | n/a | 1.84 | n/a |
| Peel force on microfibre [N/5 cm] | 0.67 | n/a | 0.34 | n/a |

TABLE 2 measurements with film backsheet material

|  | MF-55 | BioPSA 7-4560 | HL1461E | DM0110 |
|---|---|---|---|---|
| Peel force on cotton [N/5 cm] | n/a | 4.50 | 2.40 | 2.30 |
| Peel force on microfibre [N/5 cm] | n/a | 3.55 | 0.20 | 0.25 |

Peel Force Test Method

1. Peel Force on Standard Cotton Material

An article of the present invention or part thereof (hereinafter sample) comprising on its garment-facing surface the PFA (the sample and PFA being at room temperature), is placed on a rigid support with the surface with the PFA facing upward, away from the support. Then a plate having an opening, which hereinafter is called "measurement window", is placed on top of the sample's surface, which comprises the PFA. The sample dimensions are to be chosen such that the sample at least fits the measurement window having dimension of 54 mm (width)×126 mm (length). The sample is to be placed relative to the measurement window of the plate such that the measurement window is completely filled by the sample. By this, the PFA surface coverage of the part of the garment-facing surface, which is exposed through the measurement window, is about 100%. The sample is placed such that the measurement window is completely filled with PFA. The sample is fixed to the support by grips in a tight and wrinkle-free manner. Then a piece of cotton (100%), known as Weave Style no. 429W, available from Loeffler, Sitter Technic GmbH, Nettersheim, Germany, is placed on top of the surface with the PFA, which is exposed through the measurement window, such that one end of the cotton piece extends about 25 mm from the end of the measurement window with the PFA. The measurement window must be completely covered by the cotton piece. Then, a weight is placed on the thus formed sample-cotton combination for 30 seconds, such that the whole combination is covered and a weight of 26-27 g/cm$^2$ is applied, to ensure that the combination is pressed in a gentle and even manner.

Then, Zwick tensile tester (available from Zwick GmbH) is used to measure the peel force required to remove the cotton piece from the sample. Hereto, the support carrying the sample covered by the cotton piece is placed in the lower clamp of the tensile tester and the tail end of the cotton piece (the one opposite to the free 25 mm specified above) is placed in the upper clamp of the tensile tester. The Zwick tensile tester is set on a speed of 102 cm/min. Typically, the clamps are 250 mm spaced apart. It is obvious that any suitable constant rate of elongation tensile tester can be used.

Then, within 1 minute after removal of the compression weight, the tensile tester is started. The cotton piece is peeled off from the sample in a direction, which is parallel to the longitudinal dimension of the measurement window. During the peeling procedure the peel force required to peel off the cotton piece along the displacement of the upper clamp, which moved in an angle of 180° with the sample, is measured. The peel force is calculated as the average of the force peaks over a 13 cm path. The first 2.5 cm and last 3.75 cm of the measurement are not taken into account by the calculation of the peel force, to avoid influences of acceleration and deceleration.

The above test is for example done on a sample of the shape and size of a regular Always Alldays pantiliner, using a support plate with a measurement window of 54 mm (width)× 126 mm (length) and a weight of 2.1 kg with area dimensions 54 mm×140 mm. The method can be easily adjusted by the skilled person for different sample sizes.

2. Peel Force on Standard Microfibre Material

This method is a variation of the method above for PFA peel strength measurement on cotton. Such variation has been designed to measure PFA peel strength from microfibre swatches instead of rigid cotton swatches. In fact when using the microfibre swatch, it will be stretched along the test, such stretching increasing a lot the variability of the method above for cotton material. Therefore it has been designed a specific sample preparation for the microfibre material with a tape, in order to rigidify the microfibre material like the rigid cotton swatch. Once the microfibre swatch has been prepared as described below, the test will be performed using the method above for cotton by just replacing the cotton swatch with the blocked microfibre swatch.

Figure 8:
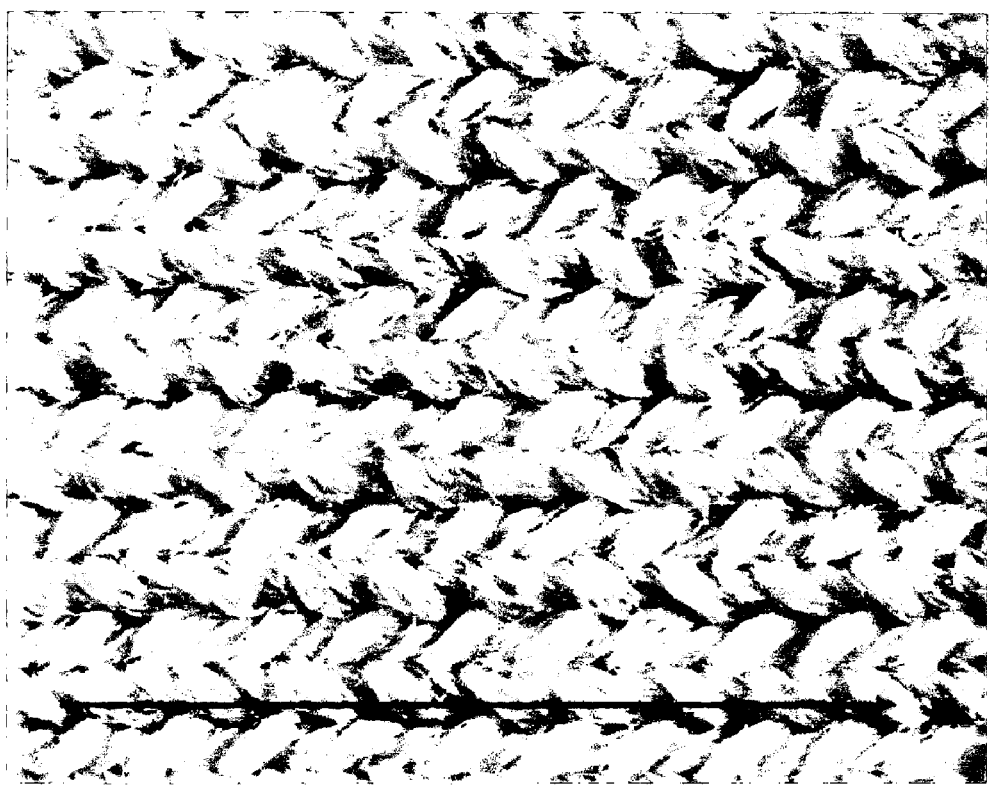
FIG. 8 shows the tape side of the standard microfibre material for use in the peel force test method herein.
Figure 9:
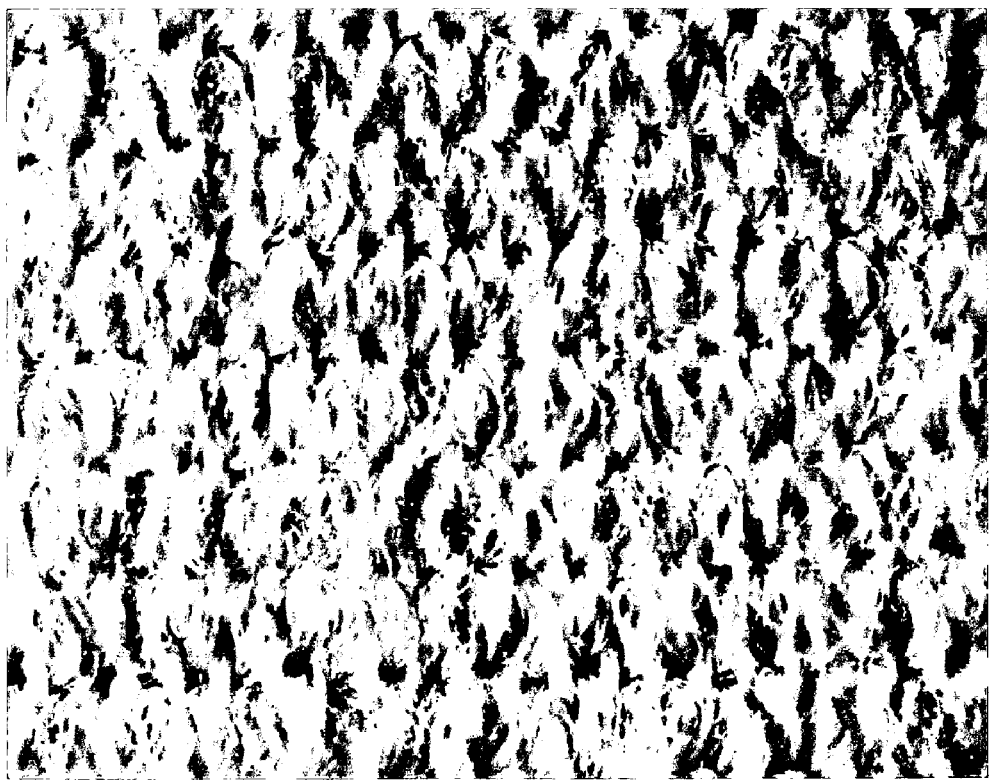
FIG. 9 shows the PFA side of the standard microfibre material for use in the peel force test method herein.

The extra tools, required for the microfibre material, are:
Tape: P42, 70 mm width. Available from H-Old s.p.a.—20010 Bareggio—MI—Italy—Via Monte Nero, 35, Tel. +39 0290360612—Fax +39 0290362186
Roller Weight: Steel cylinder having a weight of 1.14 kg and 6.5 cm wide.
Microfibre swatches: 95% nylon, 5% elastan, color white, available from Maglificio Brugnoli Giovanni Sp.A. in Busto Arsizio (Va) Italy, under the code Zaffiro B/Fast ZAFF60TN, having a thickness of 0.7 mm, a basis weight of 160 g/m$^2$, dimensions of 457 mm×76 mm, oriented along the jersey pattern direction of the fabric (indicated with the black arrow in the FIG. 8). FIG. 8 is showing the tape side of the microfibre material, i.e. the side of the microfibre material onto which the tape is attached to block the microfibre swatch: as clear from the picture, such side is the textured one showing the fish bone like pattern of the jersey knitting). The PFA side (to be attached to the PFA) is the smoothest one (see FIG. 9).

The blocked microfibre swatch will be prepared as follows:
Take a microfibre swatch and hold it so that the PFA side is on the bottom
Lay down the microfibre swatch onto a table.
Lay down the tape onto the microfibre swatch, in order to cover the swatch. The tape piece must be as long as the microfibre swatch.
Move the roller weight slowly twice at constant speed over the tape in the length direction, both times in the same sense. This will allow the tape to stick to the microfibre swatch. During the rolling, avoid additional pressure—only the weight of the roller must be applied.
The roller is only used to combine the P42 tape to the microfibre fabric.

In both test methods described hereinbefore the mean value of 10 measurements under identical conditions was used to obtain one data point.

It is obvious that the test methods disclosed herein can also be used for testing absorbent articles, which comprise PFA on their garment-facing surface in a non-continuous pattern, such as in the form of stripes or dots. In this case the article has to be arranged in respect to the measurement such that the PFA coated area, which is exposed through the measurement window, is maximized.

All documents cited in the Detailed Description of the Invention are, in relevant part, incorporated by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. In particular it is obvious to the person skilled in the art that the present invention applies to microfibre materials with inherent hydrophobicity as well as to other panty materials, which were subjected to a hydrophobic treatment. It is therefore intended to cover in the appended claims all such changes and modifications that are within the scope of this invention.

What is claimed is:

1. A disposable absorbent article for personal hygiene, said article having a wearer-facing surface and a garment-facing surface, said garment-facing surface comprising at least one adhesive A for attachment of said article to a garment of a wearer, wherein said adhesive A on said garment-facing surface provides a first peel force of at least 0.6 N per 5 cm when measured from a microfibre substrate comprising 95% nylon and 5% elaston and having a thickness of 0.7 mm and a basis weight of 160 g/m2 according to the Peel Force on Standard Microfibre Material test method.

2. The absorbent article of claim 1, wherein said garment-facing surface is covered by said adhesive A at a surface coverage of at least 30%.

3. The absorbent article of claim 1, wherein said garment-facing surface is covered by said adhesive A at a surface coverage of at from about 70% to about 100%.

4. The absorbent article of claim 1, wherein said adhesive A is present on said garment-facing surface at a basis weight of from about 1 to about 35 g/m2.

5. The absorbent article of claim 4, wherein said adhesive A is present on said garment-facing surface at a basis weight of from about 10 to about 30 g/m2.

6. The absorbent article of claim 1, wherein said adhesive A provides a first peel force of at least 0.8 N per 5 cm when measured from a microfibre substrate comprising 95% nylon and 5% elaston and having a thickness of 0.7 mm and a basis weight of 160 g/m2 according to the Peel Force on Standard Microfibre Material test method.

7. The absorbent article of claim 6, wherein said adhesive A provides a first peel force of at least 1.2 N per 5 cm when measured from a microfibre substrate comprising 95% nylon and 5% elaston and having a thickness of 0.7 mm and a basis weight of 160 g/m2 according to the Peel Force on Standard Microfibre Material test method.

8. The absorbent article of claim 1, wherein said adhesive A provides a second peel force when measured according to the Peel Force on Standard Cotton Material test method, wherein said second peel force is up to five times higher than said first peel force, when the basis weight of the cotton material tested and the basis weight of the microfibre material tested are the same.

9. The absorbent article of claim 8, wherein said adhesive A provides a second peel force when measured according to the Peel Force on Standard Cotton Material test method, wherein said second peel force is up to three times higher than said first peel force, when the basis weight of the cotton material tested and the basis weight of the microfibre material tested are the same.

10. An absorbent article for personal hygiene, said article having a wearer-facing surface and a garment-facing surface, said garment-facing surface comprising:
    a) at least one adhesive A for attachment of said article to a garment of a wearer, wherein said adhesive A on said garment-facing surface provides a first peel force of at least 0.6 N per 5 cm when measured according to the Peel Force on Standard Microfibre Material test method; and
    b) at least one additional adhesive B, wherein said adhesive B provides a first peel force of at least 0.6 N per 5 cm when measured according to the Peel Force on Standard Cotton Material test method.

11. The absorbent article of claim 10, wherein said adhesives A and B are present on said garment-facing surface at a combined basis weight of from about 1 to about 35 g/m2.

12. The absorbent article of claim 10, wherein said adhesives A and B are present on said garment-facing surface at a combined basis weight of from preferably about 10 to about 30 g/m2.

13. The absorbent article of claim 10, wherein said adhesives A and B are present on said garment-facing surface at equal basis weight.

14. The absorbent article of claim 10, wherein said adhesives A and B are present on said garment-facing surface at a combined surface coverage of from about 70 to about 100%.

15. The absorbent article of claim 10, wherein said adhesives A and B are present on said garment-facing surface at equal surface coverage.

16. The absorbent article claim 10, wherein at least one of said adhesives A and B is a hot melt adhesive and preferably both of said adhesives A and B are hot melt adhesives.

17. The absorbent article of claim 16, wherein said adhesive A is a hot melt silicone pressure-sensitive adhesive.

18. The absorbent article of claim 17, wherein said hot melt silicone pressure-sensitive adhesive A comprises (i) a silicone resin, (ii) a silicone fluid and (iii) 1 to 10% by weight based on the total weight of the silicone resin and the silicone fluid, of at least one ester having the formula:

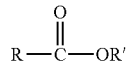

wherein R is a monovalent hydrocarbon radical having from 2 to 32 carbon atoms, and R' is a monovalent hydrocarbon radical having from 1 to 14 carbon atoms.

19. The article of claim 10, further comprising a backsheet, wherein said adhesive A and B are located on the garment-facing surface of the backsheet and/or on the garment-facing surface of the wings when in use.

* * * * *